(12) United States Patent
Lee et al.

(10) Patent No.: US 8,443,804 B2
(45) Date of Patent: May 21, 2013

(54) ADJUSTABLE VOLUME MANUAL RESUSCITATION BAG ASSEMBLY

(75) Inventors: Gary C. J. Lee, Taipei (TW); Lorence Chen, Taipei (TW); Thomas C. Loescher, Rancho Santa Fe, CA (US)

(73) Assignee: Galerned Corporation (TW)

( * ) Notice: Subject to any disclaimer, the term of this patent is extended or adjusted under 35 U.S.C. 154(b) by 442 days.

(21) Appl. No.: 12/675,966

(22) PCT Filed: Sep. 4, 2008

(86) PCT No.: PCT/US2008/075266
§ 371 (c)(1),
(2), (4) Date: Jun. 14, 2010

(87) PCT Pub. No.: WO2009/032932
PCT Pub. Date: Mar. 12, 2009

(65) Prior Publication Data
US 2011/0120472 A1    May 26, 2011

Related U.S. Application Data

(60) Provisional application No. 60/970,779, filed on Sep. 7, 2007.

(51) Int. Cl.
*A61M 16/00* (2006.01)
*A61M 16/08* (2006.01)

(52) U.S. Cl.
USPC ............ 128/205.14; 128/203.28; 128/204.28; 128/205.13; 128/205.15; 128/205.17; 128/205.18; 128/205.24; 417/472

(58) Field of Classification Search
USPC ............ 128/205.13–205.18, 203.28, 204.28, 128/207.12; 251/205–209; 417/472; 600/540, 600/541
See application file for complete search history.

(56) References Cited

U.S. PATENT DOCUMENTS

| | | | | | |
|---|---|---|---|---|---|
| 2,969,789 | A | * | 1/1961 | Morch | 128/205.14 |
| 3,396,723 | A | * | 8/1968 | Freytag | 128/205.14 |
| 3,530,856 | A | * | 9/1970 | Bird et al. | 128/200.18 |
| 3,537,450 | A | * | 11/1970 | Fox | 128/205.14 |
| 4,076,021 | A | * | 2/1978 | Thompson | 128/205.18 |
| 4,096,751 | A | * | 6/1978 | Withers et al. | 73/864.18 |
| 4,539,985 | A | * | 9/1985 | Magrath | 128/205.13 |

(Continued)

FOREIGN PATENT DOCUMENTS
WO    WO 97/01367    1/1997

OTHER PUBLICATIONS

International Search Report and Written Opinion for International Application No. PCT/US2008/07566 filed Sep. 4, 2008.

(Continued)

*Primary Examiner* — Clinton T Ostrup
*Assistant Examiner* — Christopher Miller
(74) *Attorney, Agent, or Firm* — Knobbe Martens Olson & Bear, LLP

(57) ABSTRACT

An adjustable volume control manual resuscitation bag assembly includes a resuscitation bag, a volume control knob, a traction assembly operating in response to adjustment of the control knob, and a follower assembly including a bag compression limiting member and a follower which are moved in response to operation of the traction assembly to adjust and limit the volume of gas delivered by compression of the bag.

15 Claims, 6 Drawing Sheets

U.S. PATENT DOCUMENTS

| | | | |
|---|---|---|---|
| 4,898,166 A | 2/1990 | Rose et al. | |
| 5,628,305 A | 5/1997 | Melker | |
| 5,722,394 A * | 3/1998 | Loescher | 128/205.24 |
| 5,787,880 A | 8/1998 | Swanson et al. | |
| 6,427,687 B1 | 8/2002 | Kirk | |
| 7,121,278 B2 | 10/2006 | Maguire | |

OTHER PUBLICATIONS

International Preliminary Report on Patentability for International Application No. PCT/US2008/07566 filed Sep. 4, 2008.

* cited by examiner

ADJUSTABLE VOLUME MANUAL RESUSCITATION BAG ASSEMBLY

BACKGROUND OF THE INVENTION

Volume control of manual resuscitation bags is an important feature not presently found on commercially available manual resuscitation equipment. Volume control and adjustment is especially important, and may be critical, for resuscitating infants, particularly neonatal care patients. Typical infant and neonatal resuscitation bags have a volume capacity of about 100 ml. Yet for very small patients with such limited lung capacity, it is desirable to limit the volume delivered to the infant or prenatal patient to less than 100 ml, e.g., between about 10 ml and about 60 ml or between about 20 ml and about 80 ml per bag compression. It is to such a volume controllable manual resuscitation bag assembly that the present invention is directed.

SUMMARY OF THE INVENTION

The following description is directed to a manual resuscitation bag apparatus having components capable of providing operator selection and adjustment of the volume of gas delivered to a patient with each resuscitation bag compression. In a preferred embodiment, the resuscitation bag is a bellows or accordion-type bag having a total bag capacity of about 120 ml. The bag is compressed by the operator depressing the distal end of the bag toward the proximal end of the bag.

The volume selection and adjustment components include a rotatable volume control member secured on the outside of the bag, preferably at the distal end, and volume adjustment components located within the bag. In a preferred embodiment, the volume adjustment components include a follower assembly comprising a bag compression stop member and a follower device movable axially in the bag from the distal end toward the proximal end, and traction assembly components cooperating with the volume control member for moving the follower assembly in response to rotation of the volume control member.

In a first preferred embodiment, a follower assembly is rotated by a rotatable guide member secured to the volume control member. The follower assembly is moved axially in response to a traction device cooperating with a helical track formed on the follower assembly to urge a rotating follower device axially. The guide member also cooperates with the traction device to support the follower assembly.

In a second preferred embodiment, the follower assembly does not rotate but is urged axially by a rotatable traction device secured to the volume control member, the traction device cooperating with a helical track formed on the follower assembly. A stationary guide member cooperates with the follower assembly to assist in directing its axial movement. The guide member also cooperates with the traction device to support the follower assembly position in the bag.

More specific features of the various components, configurations, assembly and operation of the apparatus will be described in the following detailed description.

DETAILED DESCRIPTION OF THE PREFERRED EMBODIMENTS

Figure 1:
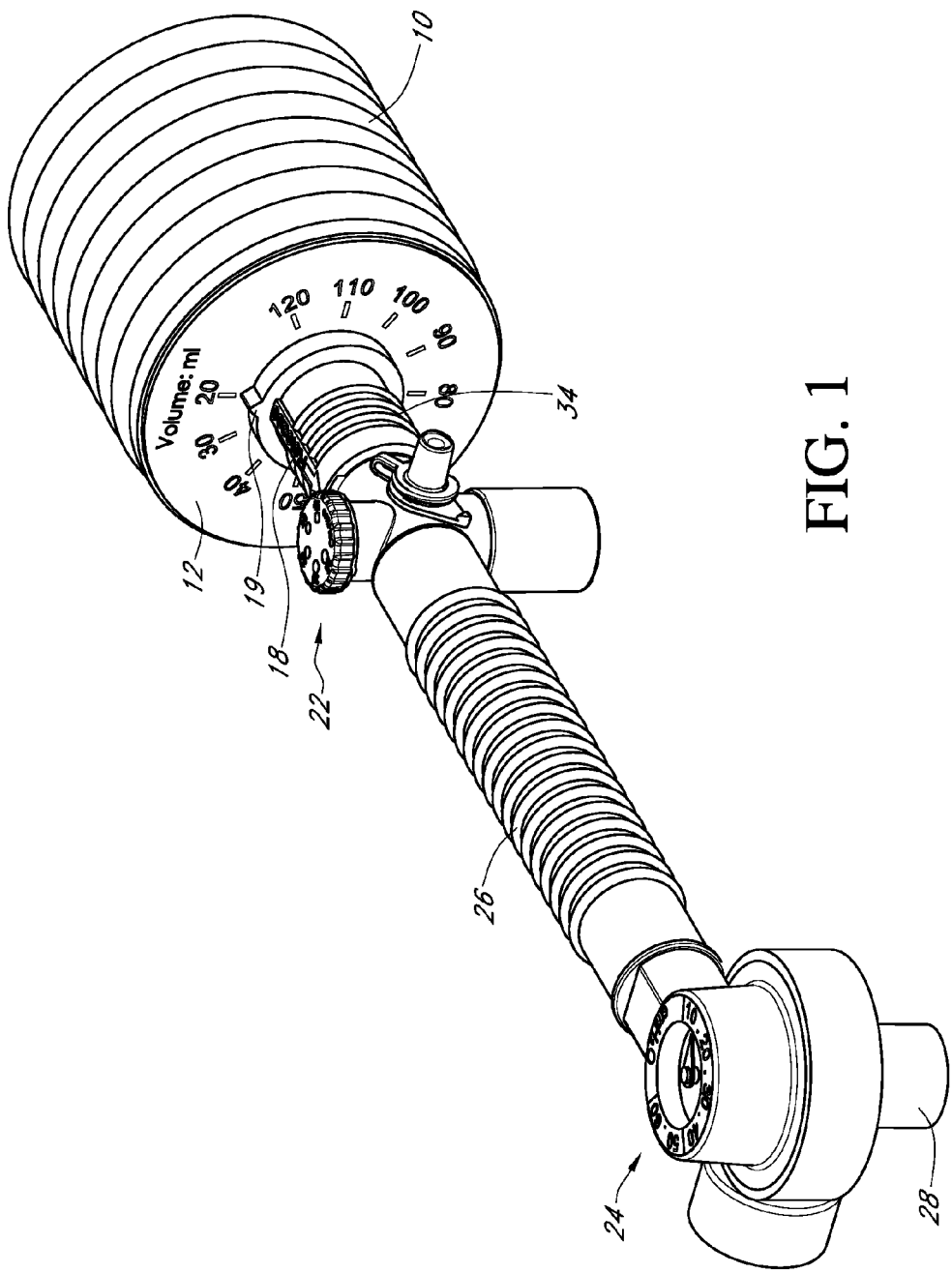
FIGS. 1 and 2 are perspective views from the proximal and distal ends of the manual resuscitation bag assembly, respectively.
Figure 2:
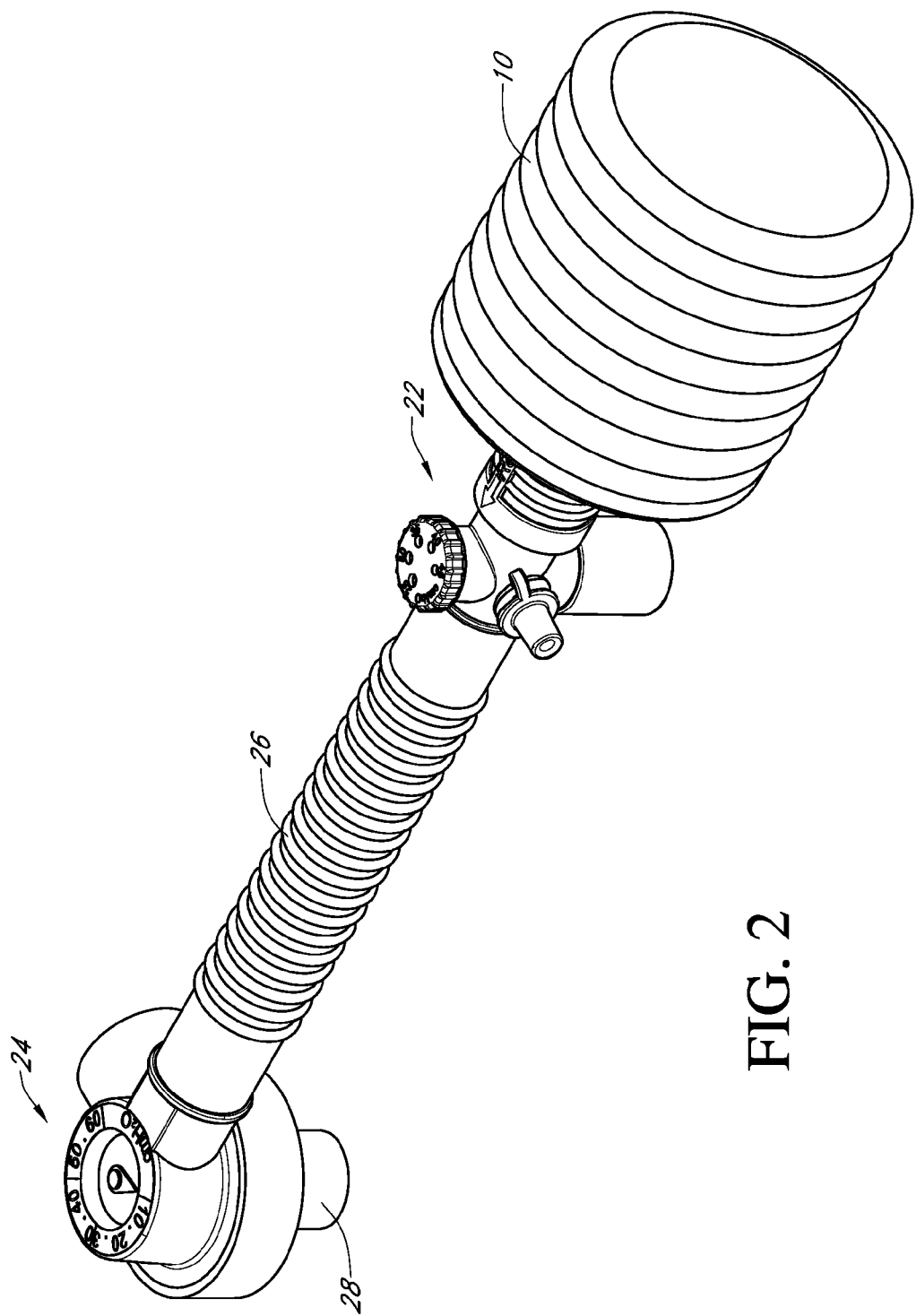
Figure 3:
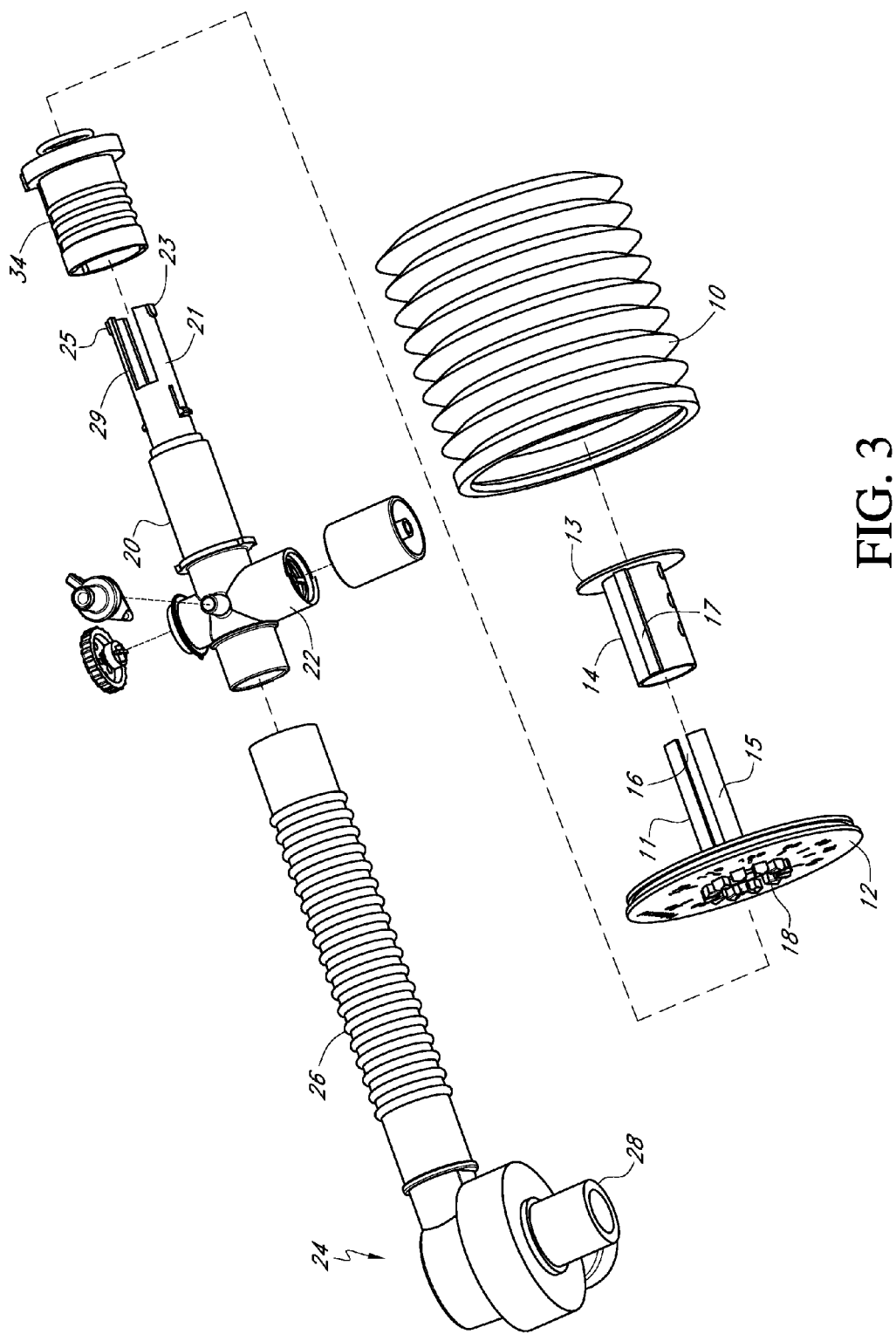
FIG. 3 is an exploded view showing components of the volume control assembly of the apparatus.
Figure 4:
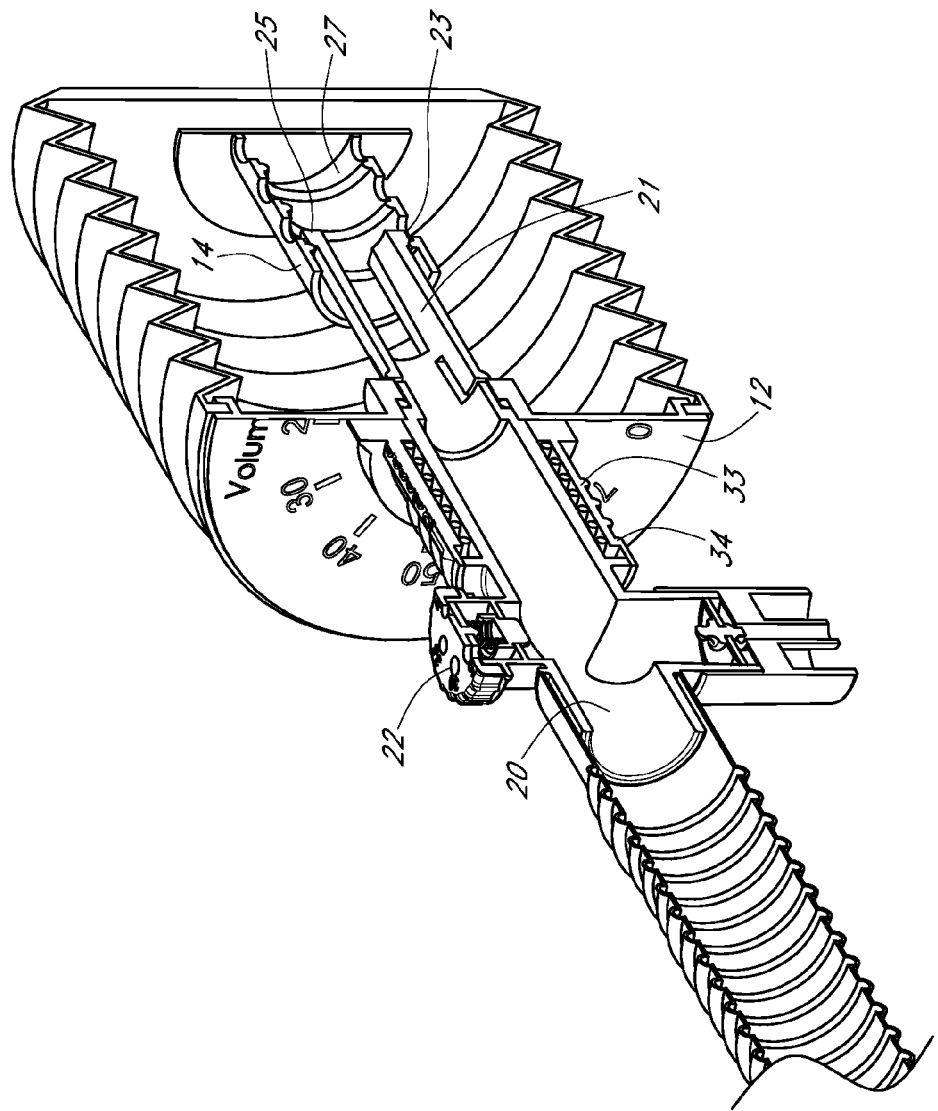
FIGS. 4 and 5 are proximal and distal sectional views, respectively, showing the internal components of the volume control and volume adjustment assemblies.
Figure 5:
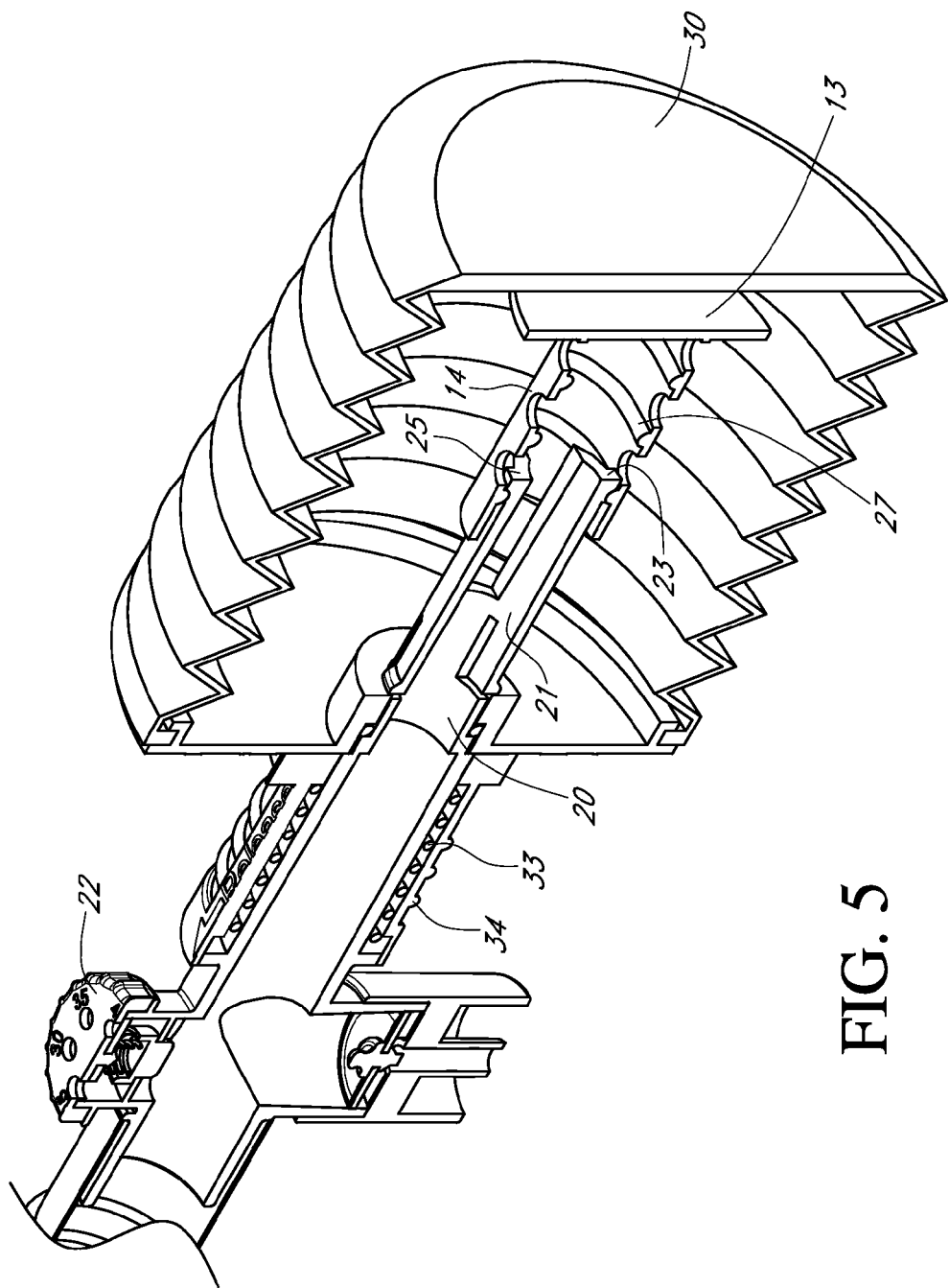
Figure 6:
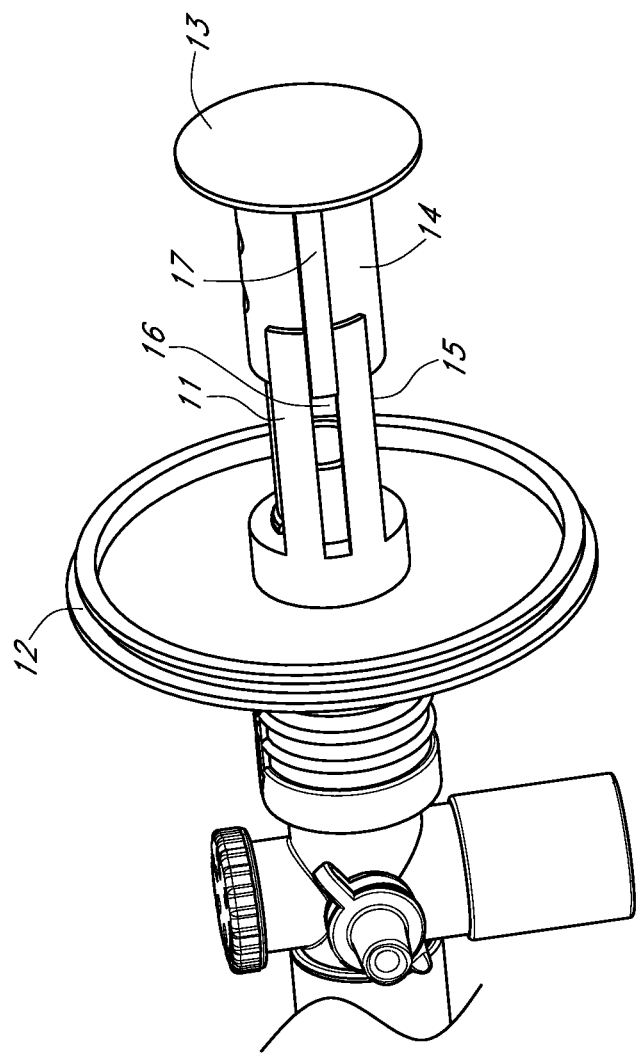
FIG. 6 is a perspective view of volume adjustment assembly components showing other features thereof.

FIGS. 1 and 2 are external views showing various components of a preferred manual resuscitation bag assembly. Major components illustrated include a resuscitation bag 10, pressure relief valve assembly 22, non-rebreathing valve assembly 24 and an extension tube 26. At the patient end of the apparatus, i.e., the proximal end, is located the non-rebreathing valve assembly 24 and a patient adapter 28. Typically, when resuscitating a patient, a face mask is used which is attached to the patient adapter 28. Details of components, designs and operation of a pressure relief valve and a non-rebreathing valve assembly are not described in further detail herein. The extension tube 26 is preferably flexible, and, for example, a corrugated gas delivery tube may be used.

The resuscitation bag 10, as shown, is preferably an accordion or bellows-type which is self-inflating and self-rebounding. The bag is manually compressed by an operator depressing the bag at the distal end 30 toward the proximal end or front of the bag, thereby displacing a volume of gas directed and delivered to the patient. The bag is preferably formed of silicon or polyurethane, although other materials such as polyethylene, polypropylene or polyvinylchloride may be used. The latter may be least preferred because of the possibility of undesirable volatile gaseous residues.

Observing also FIGS. 3-6, the volume control member 12 is rotatably secured at the proximal end of the resuscitation bag where it can be readily observed and selectively rotated by the user. The front or exposed face of the volume control member may be provided with indicia marking the different volumes to be selected and provided with lock recesses or detents 18 which cooperate with retractable volume control lock 34 to position the selected volume control member and prevent inadvertent rotation. An indicator dial 19 indicates the position of the indicia on the volume control member 12.

The volume adjustment components includes a follower assembly and a traction assembly. The traction assembly includes a guide member secured to and extending from rotatable volume control member 12 and comprises a pair of shafts 11, 15, spaced apart to define an elongated slot 16. A follower assembly comprises a compression stop plate 13 to which is secured a follower device comprising a cylindrical sleeve 14 on which is formed an elongated flange 17. Observing also FIGS. 3 and 6, flange 17 slidably engages elongated slot 16 and is movable along the slot when the volume adjustment assembly is rotated, as later explained. The pair of shafts and the slot form a guide for axial movement of the follower device 14 forward and backward (proximal and distal) within the resuscitation bag.

The traction assembly also includes a traction device configured to contact and force movement of the cylindrical sleeve 14 and compression stop plate 13 in response to rotation of the volume control member 12. In the embodiment illustrated, this operation is controlled by a helical track 27 in the form of a helical groove or recess formed on the interior surface of cylindrical sleeve 14 cooperating with lugs 23 and 25 at the ends of traction device arms 21, 29. The traction device arms extend from and are secured to gas inlet/outlet pipe 20. The traction device arms 21, 29 are stationary and are not driven by rotation of the volume control member.

In operation, as the volume control member 12 is rotated, the guide member shafts 11 and 15 cause rotation of follower device 14, and as the sleeve rotates, it is drawn axially, proximally or distally, as the helical track moves along the stationary traction assembly components. Thus, rotation of the volume control member 12 results in rotational and axial movement of stop plate 13 and follower device 14. The volume of gas displaced by compression of the distal end of the resuscitation bag is determined by the distance between the compression stop member plate 13 and the distal end of the bag. The volume selected by the user results in axial movement of the stop member plate 13 to a position which corresponds to the volume of gas which will be displaced between the compression stop plate and the distal end of the bag when the bag is compressed.

As an alternative design to that shown in the drawings and previously described, the stationary traction device may contact and operate on the outside of the follower device with the helical track formed on its exterior surface and with the guide member shafts extending into the follower device to force its rotation.

In another alternative configuration, not shown, the traction assembly comprises a traction device secured to the rotatable volume control member so that rotation of the volume control member will rotate the traction device. The traction device is provided with lugs, teeth or other protuberances received in or otherwise engaging the helical track formed on the outer surface of the follower device. The traction device may be in the form of a rotatable sleeve, or shafts or arms or equivalent components secured to and extending from the volume control plate and which rotate with the volume control plate to urge the follower assembly axially, forwardly or rearwardly, within the bag. The traction assembly also includes a stationary axial guide member rigidly secured to the gas inlet/outlet pipe. The guide member may comprise a flange or equivalent component received in an elongated slot on the interior surface of the follower device. Alternatively, the interior surface of the follower device may be provided with a flange or protuberance received in a slot formed on the guide member. In either case, in this latter described embodiment, the traction device rotates while the follower assembly does not rotate but moves forward or backward (proximally or distally) within the bag.

As previously noted, the volume control lock 34 is retractable, and preferably biased to the locking position using a compression spring 33 which urges the volume control lock in a locked position against the face of the volume control member to prevent inadvertent rotation once the operator has rotated the member to the selected volume.

In a preferred embodiment illustrated in FIG. 1, an operator may select and adjust the volume delivered with each bag compression in 10 ml increments between 20 ml and 120 ml, as shown on the face of volume control member 12. However, these volumes are by way of example only. Incremental volume adjustments as well as total bag delivery volume may be modified by various means, for example, by changing the size of the resuscitation bag, modifying the pitch of the helical track groove, changing the design or structure of the volume adjustment components, such as the distance the follower assembly moves in response to rotation of the volume control member, adjusting the length of the shafts, and/or moving the position of the compression stop plate. These as well as other variations and modifications of the different components as well as the arrangement and interaction of components of the apparatus within the purviews of the disclosure and claims herein will be understood by those skilled in the art.

What is claimed is:

1. A manual resuscitation bag assembly comprising:
   (a) a manually compressible resuscitation bag comprising an enclosed interior chamber having a gas port at a proximal end of the interior chamber, wherein said resuscitation bag is compressible to exhaust a volume of air in response to compression of an end of said bag;
   (b) an axially movable volume adjustment assembly positioned in said interior chamber comprising a follower assembly including a bag compression stop member and a follower device rigidly secured thereto and extending proximally therefrom;
   (c) an adjustable volume control member secured at or adjacent to the proximal end of said resuscitation bag and a traction assembly cooperating therewith and configured to contact and force movement of said follower assembly in response to adjustment of said volume control member; and
   (d) a gas pipe communicating with said interior chamber via said gas port and configured to direct a volume of air from said resuscitation bag in response to compression to the resuscitation bag.

2. The manual resuscitation bag assembly of claim 1 wherein said traction assembly includes a guide member comprising a plurality of shafts spaced apart to define one or more elongated slots, and wherein said follower device includes one or more flanges received in one or more of said slots, and wherein movement of said shafts forces movement of said follower device along said guide member.

3. The manual resuscitation bag assembly of claim 1 wherein said traction assembly includes a stationary traction device configured to cooperate with said follower device to direct axial movement of the follower device.

4. The manual resuscitation bag assembly of claim 3 wherein said follower device cooperates with said traction assembly and rotates in response to rotation of said volume control member.

5. The manual resuscitation bag assembly of claim 4 wherein said follower device includes a helical track.

6. The manual resuscitation bag assembly of claim 5 wherein said helical track comprises a helical recess, and wherein said traction member includes one or more lugs received in said helical recess.

7. The manual resuscitation bag assembly of claim 6 wherein said follower device comprises a cylindrical sleeve, and wherein said helical track is formed along the interior of said cylindrical sleeve.

8. The manual resuscitation bag assembly of claim 7 further comprising traction member having an elongated stationary shaft extending within said cylindrical sleeve, and whereby rotation of said volume control member causes rotation of said follower device and axial movement thereof along said traction member.

9. The manual resuscitation bag assembly of claim 3 wherein said follower device comprises a cylindrical sleeve having a helical track formed along the exterior thereof, and wherein said traction assembly includes an elongated traction member extending along the exterior surface of said follower device and having one or more lugs received in said helical track.

10. The manual resuscitation bag assembly of claim 9 wherein said elongated traction member is rotatable in response to rotation of said volume control member.

11. The manual resuscitation bag assembly of claim 1 including a locking member configured for selectively locking said volume adjustment member.

12. The manual resuscitation bag assembly of claim 1 including a flexible tube having a first end communicating with said gas pipe and a patient connector attached to a second end of the gas pipe.

13. The manual resuscitation bag assembly of claim 12 including a pressure relief valve.

14. The manual resuscitation bag assembly of claim 12 including a one-way non-rebreathing valve cooperating with said patient connector.

15. The manual resuscitation bag assembly of claim 1 wherein said resuscitation bag comprises a bellows bag.

\* \* \* \* \*

UNITED STATES PATENT AND TRADEMARK OFFICE
CERTIFICATE OF CORRECTION

PATENT NO. : 8,443,804 B2
APPLICATION NO. : 12/675966
DATED : May 21, 2013
INVENTOR(S) : Gary C. J. Lee et al.

It is certified that error appears in the above-identified patent and that said Letters Patent is hereby corrected as shown below:

Title Page (Item 73, Assignee), at line 1, Change "Galerned" to --Galemed--.

Signed and Sealed this
Twelfth Day of November, 2013

Teresa Stanek Rea
*Deputy Director of the United States Patent and Trademark Office*